United States Patent [19]

Lecoufle et al.

[11] Plant 4,871

[45] Aug. 3, 1982

[54] ORCHID PLANT

[75] Inventors: Maurice Lecoufle; Michel Vacherot, both of Boissy St. Leger, France

[73] Assignee: Les Petite Fils et Fils de Vacherot & Lecoufle, Boissy St. Leger, France

[21] Appl. No.: 151,944

[22] Filed: May 21, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new variety of orchid plant of the yellow class distinguished by an abundant production of flowers of good size usually borne in a group of two to four flowers well arranged on the spike and with an autumn flowering period, a strong habit of plant growth, excellent texture and substance of the flower petals and sepals, and a distinctive and attractive lemon yellow color of the petals and sepals contrasting with the velvet of a ruby red labellum.

2 Drawing Figures

BACKGROUND OF THE NEW PLANT

Our new variety of orchid plant originated as a seedling of the variety Laeliocattleya Ocarina which resulted from the cross of Lc. Edgard Van Belle×Lc. Amber Glow. This cross was made by us at our greenhouses in Boissy St. Leger, France, with the object of obtaining a new orchid variety having improved flower shape and color, large size and good flower production. This objective is believed to be fully achieved in the new plant which we have reproduced by meristem propagation at Boissy St. Leger through successive generations, which have shown that the distinctive features of the new plant hold true from generation to generation and appear to be firmly fixed.

DESCRIPTION OF THE DRAWING

Our new variety of orchid plant is illustrated by the accompanying hand painted drawing which shows a face view of the flower in full color, and by a second drawing which shows the general dimensions and form of the flower.

DESCRIPTION OF THE NEW PLANT

The following is a detailed description of our new orchid plant with color designations according to The R.H.S. Colour Chart produced and published by The Royal Horticultural Society of London, England.

THE PLANT

Origin: Seedling of Lc. Ocarina (unpatented).

Parentage:

*Seed parent.*—Lc. Edgard Van Belle (unpatented).

*Pollen parent.*—Lc. Amber Glow (unpatented).

Classification:

*Botanic.*—Laeliocattleya hybrid.

*Commercial.*—Lc. mericlone.

Form: Herbaceous and well branched.

Foliage: The leaves are arched, but otherwise typical of Laeliocattleya varieties, smooth and slightly rounded. They are of normal green color.

Size of leaf:

*Length.*—27 cm.

*Width.*—7 cm.

Bulbs:

*Length.*—From 17 cm. to 25 cm.

*Width.*—6 mm. at the base, 18 to 25 mm. at the medium point and 15 mm. at the top.

Sheath:

*Length.*—15 cm.

*Width.*—3.2 cm.

Number: 5 to 8 bulbs with leaves, but can produce an indefinite number of them.

Rhisome: 3 cm. in length and appearing between pseudobulbs.

THE FLOWER

Blooming season: September–October at the latitude of Paris, France, or in the Northern Hemisphere.

Blooming habit: Each spike usually bears flowers in clusters of two to four. The petals and sepals are of good shape and substance and the border of the labellum is delicately fringed and closed around the gynostemium.

Size:

*The flower.*—Width — about 13.5 cm. Height — about 13.5 cm.

*The petals.*—Width — about 6 cm. Length — about 7 cm.

*Sepals.*—Width — about 2.5 cm. Length — about 6.6 cm.

*Dorsal sepal.*—Width — about 2.5 cm. Length — about 7.2 cm.

*The labellum.*—Width — about 5.8 cm. Height — about 6.8 cm.

*Gynostemium.*—Length — about 3.7 cm.

Color:

*The petals.*—From Lemon Yellow 13A to Aureolin 12C.

*Sepals.*—From Buttercup Yellow 15A to Chrome Yellow 15C.

*Labellum.*—Ruby Red 61A with Cadmium Orange 23A veins around the gynostemium.

We claim:

1. The new and distinct variety of orchid plant substantially as herein shown and described, characterized by a strong habit of plant growth and abundant production of flowers having petals and sepals of excellent texture and substance and a distinctive lemon yellow color of the petals and sepals contrasting with a ruby red labellum.

* * * * *

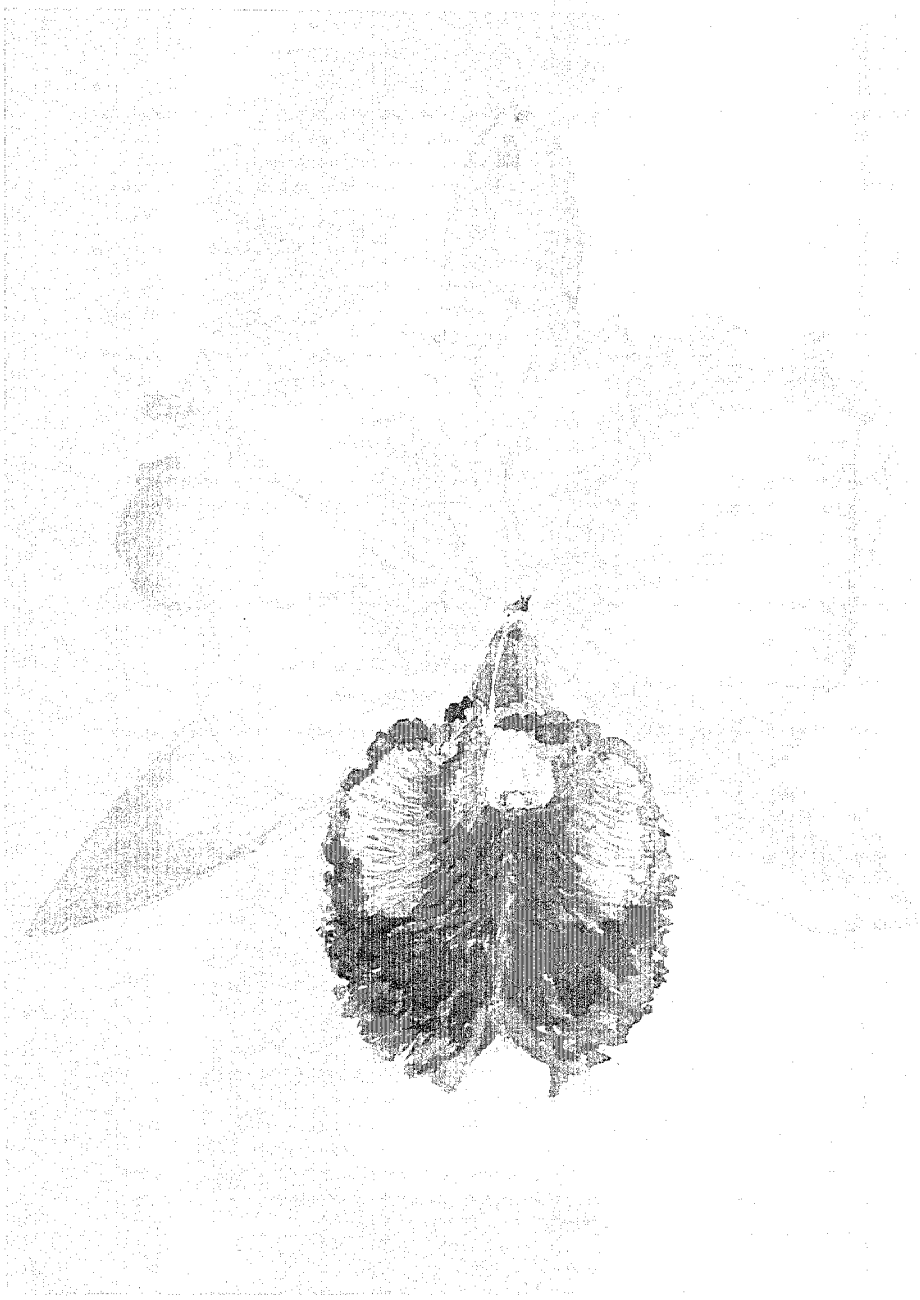

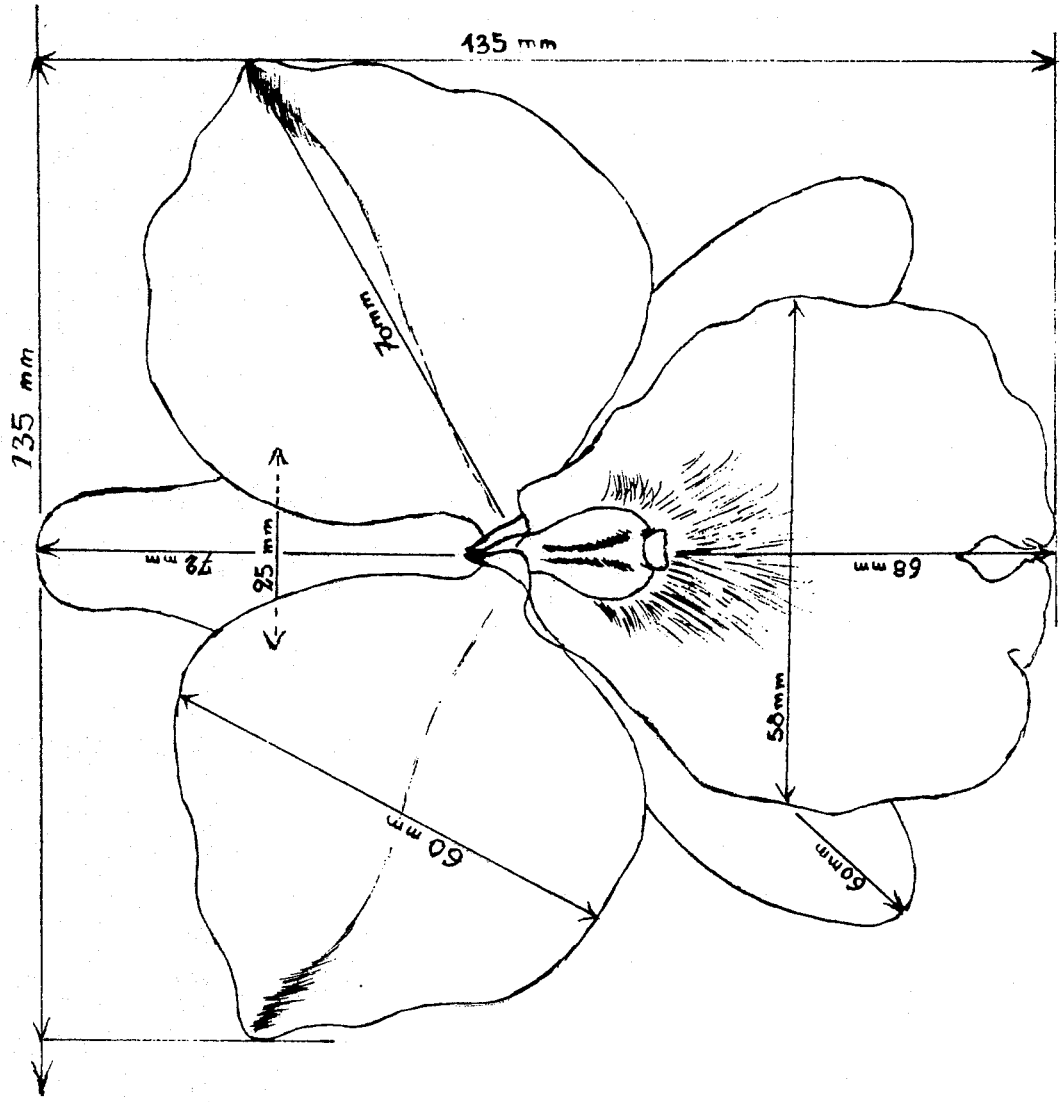
135 mm
135 mm
70mm
78 mm
25 mm
60 mm
68 mm
58mm
60mm